United States Patent
Byrd et al.

(10) Patent No.: US 12,102,319 B2
(45) Date of Patent: Oct. 1, 2024

(54) METHODS FOR MEASURING TISSUE DEFECTS

(71) Applicants: Smith & Nephew, Inc., Memphis, TN (US); Smith & Nephew Orthopaedics AG, Zug (CH); Smith & Nephew Asia Pacific Pte. Limited, Singapore (SG); J. W. Thomas Byrd, Nashville, TN (US)

(72) Inventors: J. W. Thomas Byrd, Nashville, TN (US); Timothy Young, Natick, MA (US); Michael Thyden, Billerica, MA (US); Marc J. Balboa, Hopkinton, MA (US)

(73) Assignees: Smith & Nephew, Inc., Memphis, TN (US); Smith & Nephew Orthopaedics AG (CH); Smith & Nephew Asia Pacific Pte. Limited, Singapore (SG)

( * ) Notice: Subject to any disclaimer, the term of this patent is extended or adjusted under 35 U.S.C. 154(b) by 405 days.

(21) Appl. No.: 17/553,006

(22) Filed: Dec. 16, 2021

(65) Prior Publication Data

US 2022/0192652 A1 Jun. 23, 2022

Related U.S. Application Data

(60) Provisional application No. 63/126,771, filed on Dec. 17, 2020.

(51) Int. Cl.
*A61B 17/04* (2006.01)
*A61B 17/17* (2006.01)
(Continued)

(52) U.S. Cl.
CPC ...... *A61B 17/0401* (2013.01); *A61B 17/0491* (2013.01); *A61B 17/1796* (2013.01);
(Continued)

(58) Field of Classification Search
CPC ............ A61B 17/0401; A61B 17/0491; A61B 17/1796; A61B 17/0485; A61B 17/16; A61B 17/17; A61B 17/04; A61B 17/0469; A61B 17/0482; A61B 17/0483; A61B 17/0487; A61B 17/06166; A61B 17/7022; A61B 17/7053; A61B 2090/061; A61B 2017/0409; A61B 2017/0496; A61B 2017/0618; A61B 2017/0411; A61B 2017/0414; A61B 2017/0446;
(Continued)

(56) References Cited

U.S. PATENT DOCUMENTS 9,814,455 B2 * 11/2017 Dooney, Jr. ........ A61B 17/0401
10,085,739 B2 * 10/2018 Dooney, Jr. ........ A61B 17/0401

* cited by examiner

*Primary Examiner* — Marcela I. Shirsat
(74) *Attorney, Agent, or Firm* — ArentFox Schiff LLP; Joseph M. Maraia; Marlo Schepper Grolnic

(57) ABSTRACT

Methods for measuring tissue defects include the use of a suture anchor, a drill guide, a needle driver, and a ruler. Using the drill guide, the surgeon extends the suture attached to an implanted anchor between the first and second ends of the defect. The surgeon then attaches a needle driver to the suture extending from the proximal end of the drill guide. Finally, the surgeon retracts the suture back through the drill guide and measures the distance between the needle driver and the proximal end of the drill guide to determine a length of a graft needed to repair the defect.

16 Claims, 6 Drawing Sheets

(51) Int. Cl.
*A61B 17/56* (2006.01)
*A61B 90/00* (2016.01)

(52) U.S. Cl.
CPC ... *A61B 2017/0409* (2013.01); *A61B 17/0469* (2013.01); *A61B 2017/0488* (2013.01); *A61B 2017/0496* (2013.01); *A61B 2017/564* (2013.01); *A61B 2017/565* (2013.01); *A61B 2090/061* (2016.02)

(58) Field of Classification Search
CPC .... A61B 2017/0464; A61B 2017/0466; A61B 2017/0488; A61B 2017/1142; A61B 2017/564; A61B 2017/565
USPC ....... 606/96, 53, 60, 300, 304, 74, 86 R, 87, 606/88, 97, 98
See application file for complete search history.

METHODS FOR MEASURING TISSUE DEFECTS

CROSS-REFERENCE TO RELATED APPLICATIONS

This application claims priority to and benefit of U.S. Provisional Application No. 63/126,771, filed Dec. 17, 2020, entitled GRAFT MEASUREMENT TECHNIQUE, the contents of which are incorporated herein by reference in their entirety for all purposes.

FIELD

This disclosure relates generally to surgical repairs and, more particularly, to methods for measuring tissue defects during surgical repair.

BACKGROUND

Many surgical procedures, such as hip labral repair, require the use of a graft to repair a segment of damaged tissue, or "defect." In such procedures, a surgeon needs to measure the defect before creating an appropriately sized graft that the surgeon can use to repair the defect. A critical component such repair includes accurately matching the graft length to the patient's native anatomy. A mismatch between the graft length and the patient's anatomy can cause the graft to be too tight or too loose or create the need for additional operation time. These issues make fixation of the graft and the overall success of the repair more challenging.

Current techniques for measuring defects have inherent problems. For example, a surgeon may use an instrument already used in the repair with a known width (such as a burr) to march along the defect length. With this technique, the surgeon visually estimates the size of the defect, with results that may not be accurate. Alternatively, a surgeon may use a straight, rigid or semi-rigid measuring tool to measure the defect. However, because many defects are contoured, this method also gives less accurate results. Finally, a surgeon may use more specialized defect measuring tools for increased accuracy. However, use of these tools may add extra time and costs to the surgery, since the surgery requires additional steps and instruments.

SUMMARY

This disclosure describes methods for measuring tissue defects more quickly and accurately than current techniques, advantageously using instruments already selected for the repair. For example, a surgeon can carry out the method using a suture anchor, a drill guide, a needle driver, and a ruler. Using the drill guide, the surgeon extends the suture attached an implanted anchor between the first and second ends of the defect. The surgeon then attaches a needle driver to the suture extending from the proximal end of the drill guide. Finally, the surgeon retracts the suture back through the drill guide and measures the distance between the needle driver and the proximal end of the drill guide to determine a length of a graft needed to repair the defect. Advantageously, unlike current measuring tools, the flexible suture can follow the contours of the defect to accurately mark its length.

Examples of the methods of this disclosure may include one or more of the following, in any suitable combination.

In examples, a method of measuring a distance between first and second locations in tissue of this disclosure include placing a distal end of a cannula against a first location in tissue. The first location is the site of a bone hole. An anchor having a body and a flexible strand is inserted into the bone hole such that the flexible strand extends from the body through the cannula and exits the proximal end of the cannula. The distal end of the cannula is placed against a second location in the tissue such that a first portion of the flexible strand extends between the first location and the second location. The first portion of the flexible strand has a first length. A clip member is attached to the flexible strand at the proximal end of the cannula. The distal end of the cannula is replaced against the first location and the flexible strand is tensioned such that a second portion of the flexible strand extends between the proximal end of the cannula and the clip member. The second portion of the flexible strand has a second length equal to the first length. Using a measuring tool, a measurement of the second length is determined. The measurement corresponds to a distance between the first and second locations in the tissue.

In examples, the method further includes inserting the anchor through the cannula from a proximal end to the distal end of the cannula into the bone hole at the first location. In examples, the method further includes inserting a capture member through the cannula from a proximal end to the distal end of the cannula to retrieve the flexible strand through the cannula. In examples, the cannula is a drill guide or a suture passer. In examples, the method further includes securing the body of the anchor in the bone hole. In examples, the body of the anchor is made of suture, and securing the body of the anchor in the bone hole includes tensioning the flexible strand to change the body from a first configuration, in which a width of the body is less than a width of the bone hole, to a second configuration, in which the width of the body is greater than the width of the bone hole, forming an interference fit between the body and the bone hole. In examples, the flexible strand is a suture. In examples, the clip member is a needle driver or hemostat forceps. In examples, the measuring tool is a ruler or a graduated surgical marker. In examples, the first location is at a first end of a defect in the tissue and the second location is at a second end of the defect in the tissue.

In other examples, a method of measuring a distance between first and second locations in tissue of this disclosure include placing a distal end of a cannula against a first location in tissue. A flexible member is inserted through the cannula from a proximal end to the distal end of the cannula such that a first portion of the flexible member extends from the first location to a second location in the tissue. The first portion of the flexible member has a first length. A clip member is attached to the flexible member at the proximal end of the cannula. The flexible member is pulled through the cannula such that a second portion of the flexible member extends between the proximal end of the cannula and the clip member. The second portion of the flexible member has a second length equal to the first length. Using a measuring tool, a measurement of the second length is determined. The measurement corresponds to a distance between the first and second locations in the tissue. In further examples, the cannula is a suture passer. In examples, the flexible member is a wire loop. In examples, the clip member is a needle driver or hemostat forceps. In examples, the first location is at a first end of a defect in the tissue and the second location is at a second end of the defect in the tissue.

In yet other examples, a construct for measuring a distance between first and second locations in tissue of this disclosure includes a cannula having a proximal end. The construct also includes an anchor having a body and a flexible strand. The body is insertable into a bone hole at a first location such that the flexible strand extends from the body through the cannula and exits the proximal end of the cannula. A first portion of the flexible strand is extendable between the first location and a second location. The first portion of the flexible strand has a first length. The construct also includes a clip member attachable to the flexible strand at the proximal end of the cannula. The flexible strand is further tensionable such that a second portion of the flexible strand is extendable between the proximal end of the cannula and the clip member. The second portion of the flexible strand has a second length equal to the first length. The construct further includes a measuring tool for determining a measurement of the second length. The measurement corresponds to a distance between the first and the second location. In examples, the cannula is a drill guide or a suture passer. In examples, the clip member is a needle driver or hemostat forceps. In examples, the measuring tool is a ruler or a graduated surgical marker.

A reading of the following detailed description and a review of the associated drawings will make apparent the advantages of these and other features. Both the foregoing general description and the following detailed description serve as an explanation only and do not restrict aspects of the disclosure as claimed.

BRIEF DESCRIPTION OF THE DRAWINGS

Reference to the detailed description, combined with the following figures, will make the disclosure more fully understood, wherein.

DETAILED DESCRIPTION

Figure 1A:
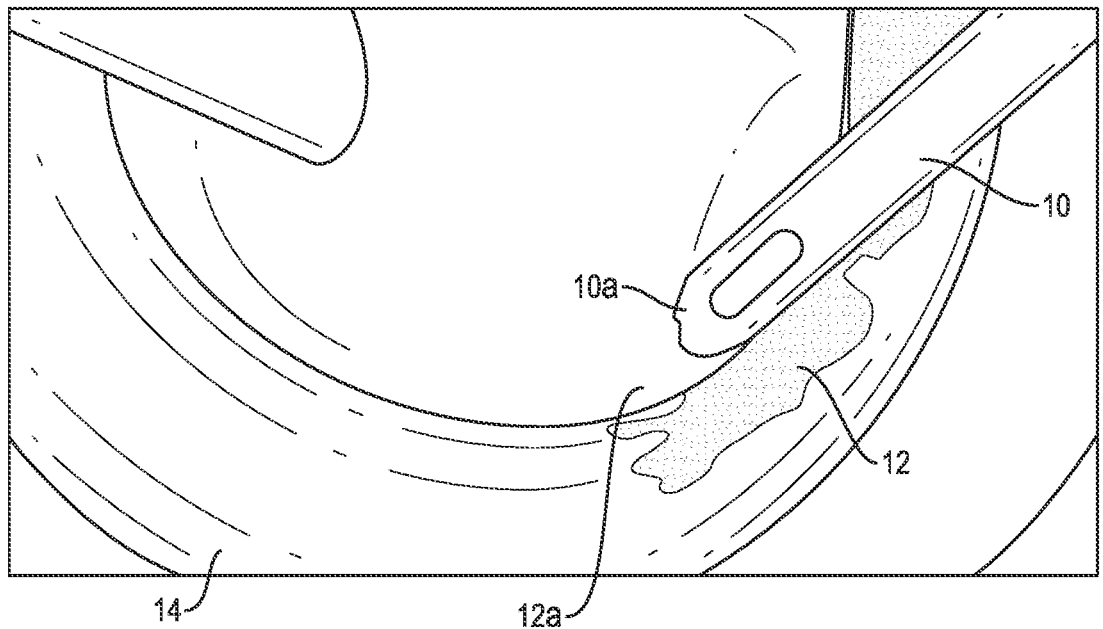
FIGS. 1A-I illustrate a first example of the method of this disclosure for measuring a tissue defect.

In the following description, like components have the same reference numerals, regardless of different illustrated examples. To illustrate examples clearly and concisely, the drawings may not necessarily reflect appropriate scale and may have certain features shown in somewhat schematic form. The disclosure may describe and/or illustrate features in one example, and in the same way or in a similar way in one or more other examples, and/or combined with or instead of the features of the other examples.

In the specification and claims, for the purposes of describing and defining the invention, the terms "about" and "substantially" represent the inherent degree of uncertainty attributed to any quantitative comparison, value, measurement, or other representation. The terms "about" and "substantially" moreover represent the degree by which a quantitative representation may vary from a stated reference without resulting in a change in the basic function of the subject matter at issue. Open-ended terms, such as "comprise," "include," and/or plural forms of each, include the listed parts and can include additional parts not listed, while terms such as "and/or" include one or more of the listed parts and combinations of the listed parts.

FIGS. 1A-I illustrate a first example of the method of this disclosure for measuring a tissue defect in a surgical repair. In examples, the defect is a labral defect and the surgical repair is a labral repair. However, the disclosure contemplates other types of defects in other types of repairs, such as superior capsular reconstruction in the shoulder.

Figure 1B:
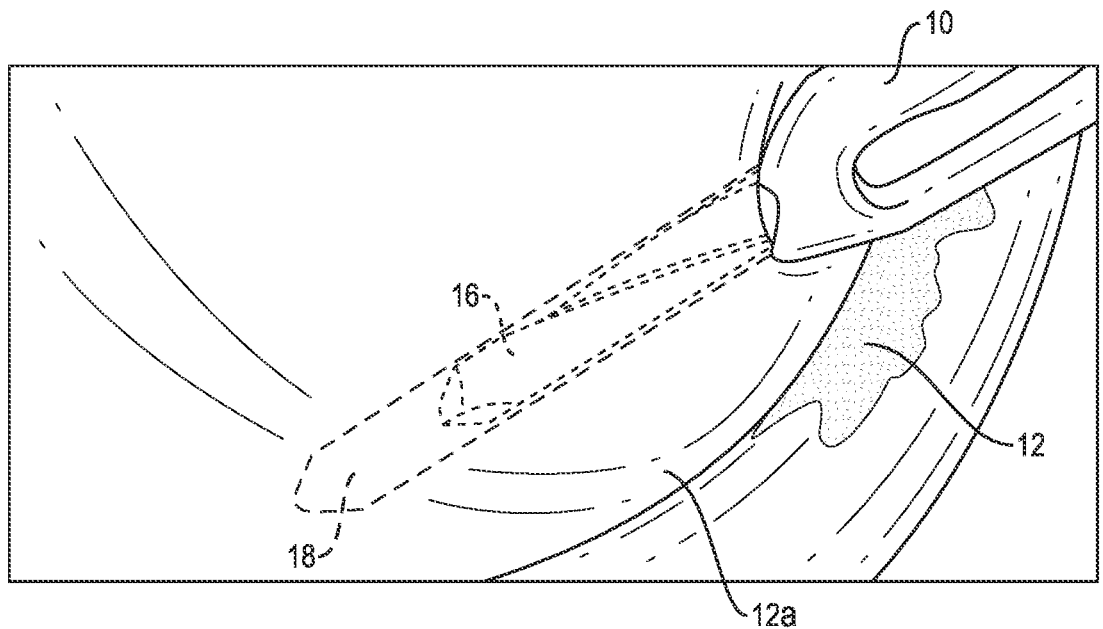
Figure 1C:
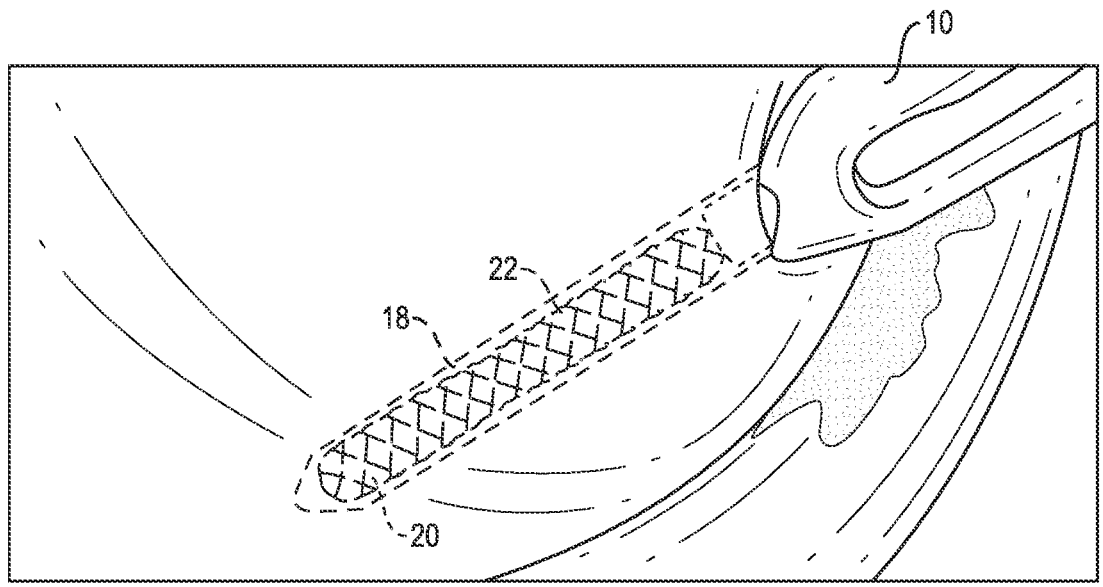
Figure 1D:
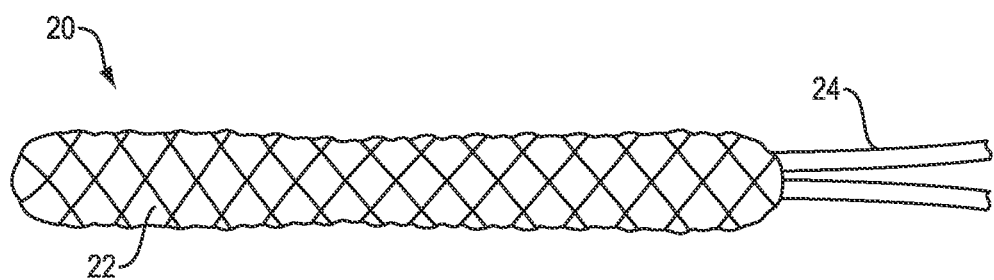

Initially, as shown in FIG. 1A, the surgeon contacts the distal end 10a of a cannula 10 against the first end 12a of a defect 12 in tissue 14. In the example of FIG. 1A, the cannula 10 is a drill guide. However, the disclosure contemplates any suitable type of cannulated instrument, including a series of cannulated instruments disposed around, within, and/or axially to one another. As shown in FIG. 1B, the surgeon then inserts a drill 16 through the cannula 10 to create a bone hole 18 at the first end 12a of the defect 12. As shown in FIG. 1C, the surgeon then inserts an anchor 20 through the cannula 10 into the bone hole 18. In examples, the anchor 20 comprises a soft anchor body 22 (for example, made of suture material) with a flexible strand 24 (for example, a suture) attached to the anchor body 22, as shown in FIG. 1D. Non-limiting examples of soft-bodied anchors are disclosed in U.S. Pat. No. 9,962,149 to ArthroCare Corporation (Austin, TX), the contents of which are incorporated herein by reference. However, the disclosure also contemplates the use of rigid or semi-rigid anchors comprising a body and a flexible strand attached to the body.

Figure 1E:
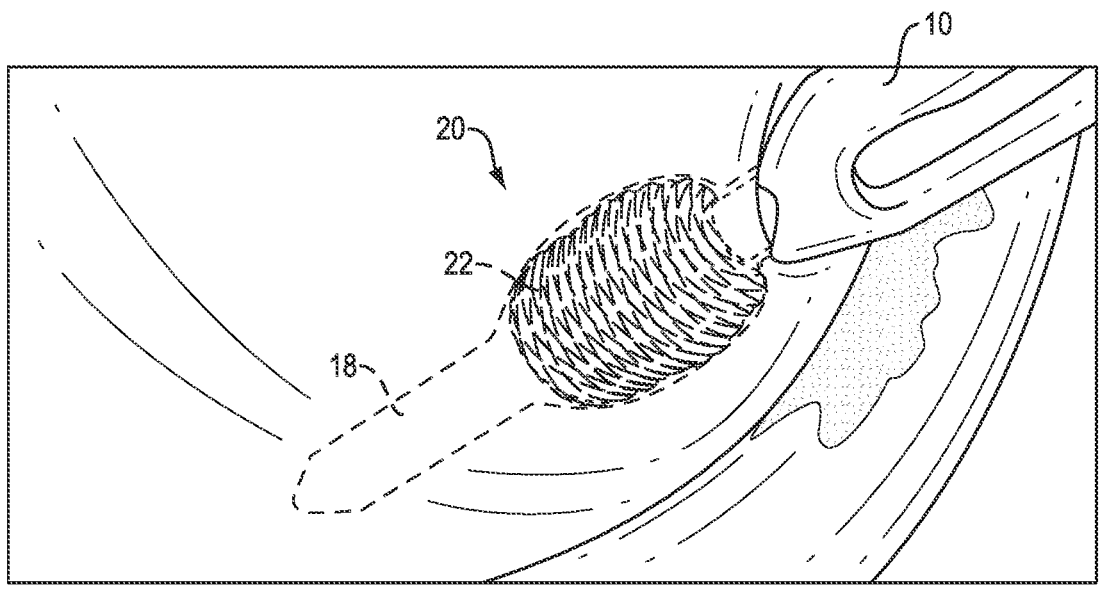

In examples, shown in FIG. 1E, the surgeon then secures the anchor 20 to the bone hole 18 by placing tension on the flexible strand 24 extending through the cannula 10 and exiting a proximal end of the cannula 10 (not shown) outside of the patient's body. Because of the nature of the attachment of the flexible strand 24 to the anchor body 22, the tensioning of the flexible strand 24 changes a configuration of the anchor body 22. Specifically, the tensioning changes the anchor body 22 from a first configuration, in which a width of the anchor body 22 is less than a width of the bone hole 18 (FIG. 1C), to a second configuration, in which a width of the anchor body 22 is greater than a width of the bone hole 18 (FIG. 1E). This change in configuration forms an interference fit between the anchor body 22 and the bone hole 18. However, the disclosure contemplates other methods of securing the anchor 20 to the bone hole 18, such as screwing or pounding.

Figure 1F:
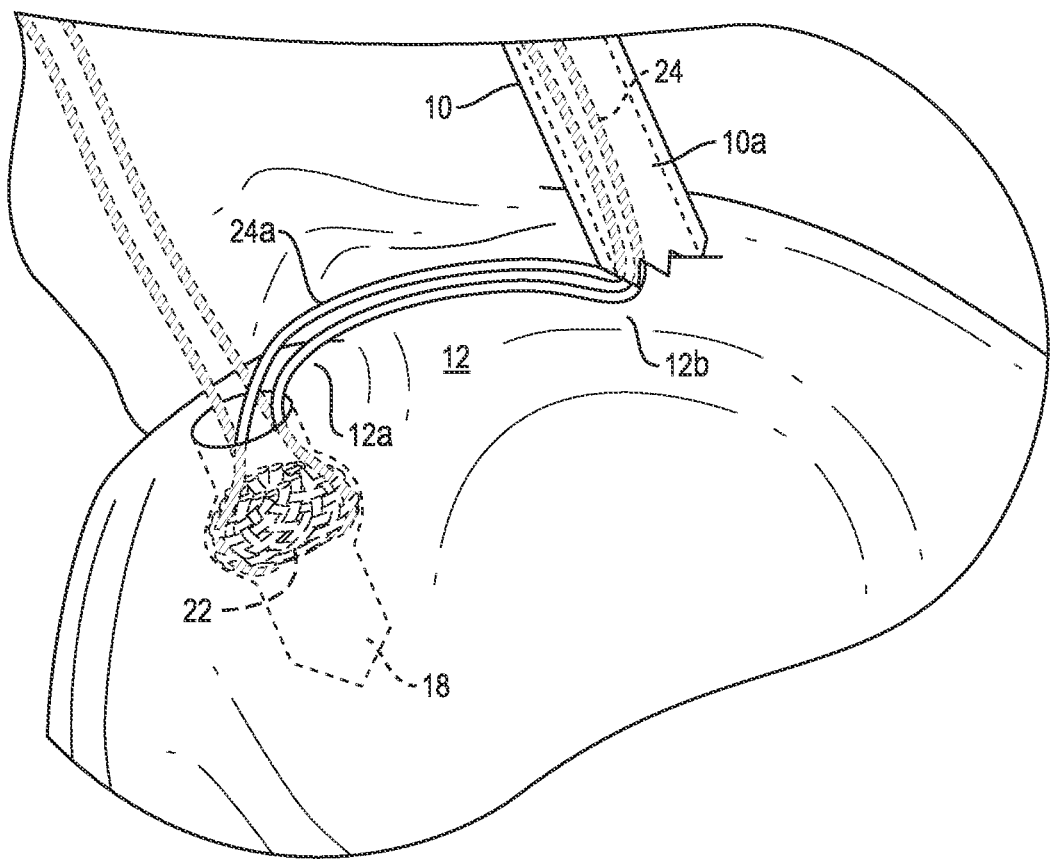
Figure 1G:
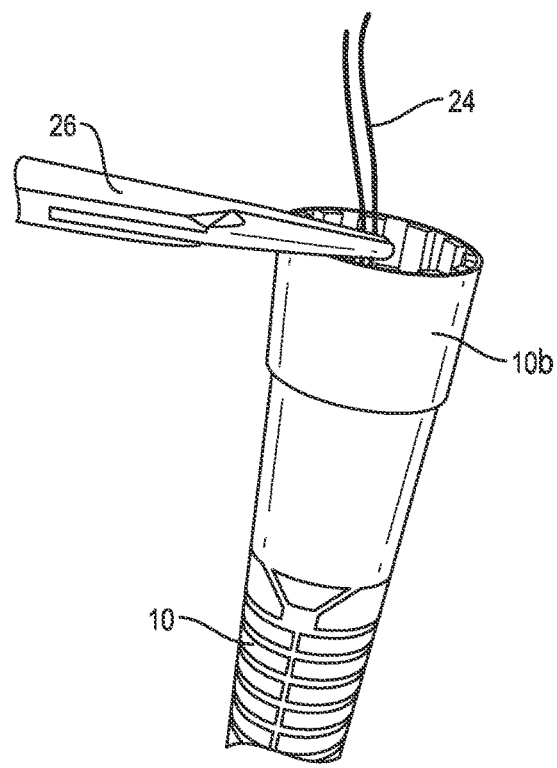
Figure 1I:
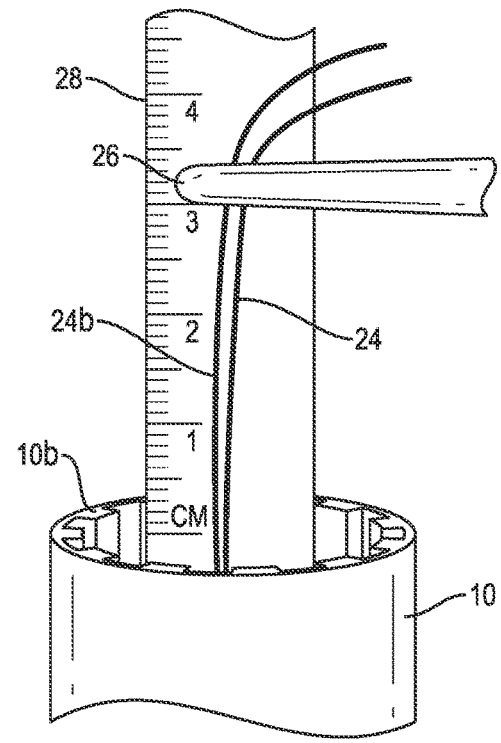
Figure 1H:
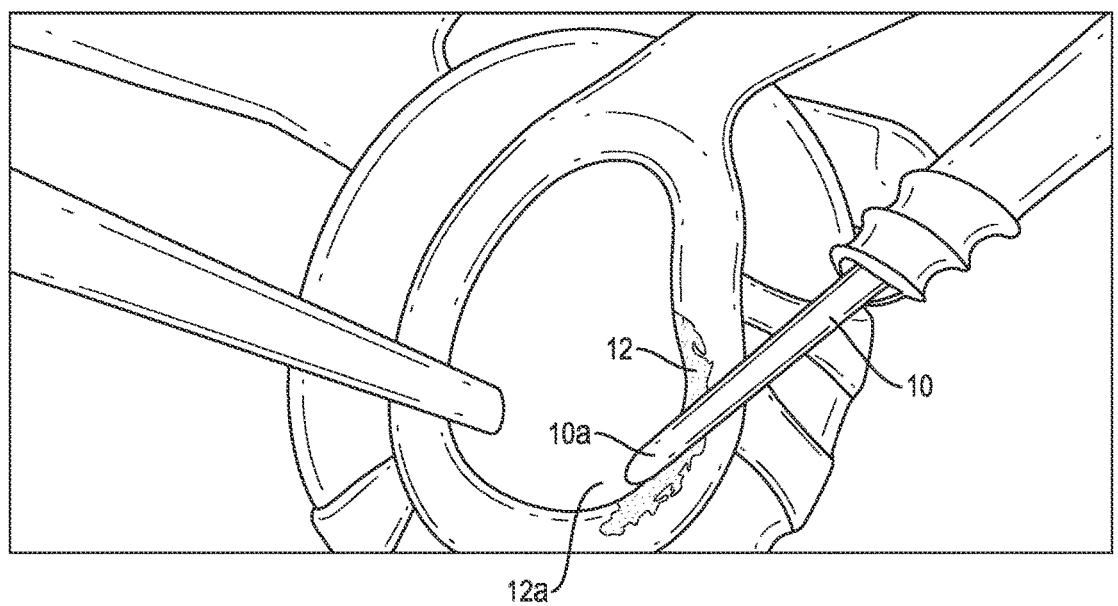

Turning now to FIG. 1F, with the anchor body 22 secured in the bone hole 18 and the flexible strand 24 extending through the cannula 10, the surgeon places the distal end 10a of the cannula 10 at the second end 12b of the defect 12 such that a first portion 24a of the flexible strand 24 extends between the first end 12a and the second end 12b of the defect 12. The surgeon takes care to account for an outer diameter of the cannula 10 when placing the cannula 10 at the second end 12b of the defect 12 such that the flexible strand 24 accurately spans the entire length and contour of the defect 12. As shown in FIG. 1G, the surgeon then attaches a clip member 26 to the flexible strand 24 extending from the proximal end 10b of the cannula 10 outside of the patient's body. In examples, the clip member 26 is a needle driver, hemostat forceps, or other suitable instrument already used in the repair. The disclosure also contemplates that the surgeon could mark the suture with a surgical marker instead of attaching a clip member. As shown in FIG. 1H, the surgeon then places the distal end 10a of the cannula 10 back to the first end 12a of the defect 12 and tensions the flexible strand 24 at the proximal end 10b of the cannula 10 (FIG. 1I). In this way, a second portion 24b of the flexible strand 24 extends between the proximal end 10b of the cannula 10 and the clip member 26. This second portion 24b of the flexible strand 24 is equal in length to the first portion 24a. The surgeon can measure the second portion 24b with a measuring tool 28, such as a ruler or graduated surgical marker. The surgeon can now use this measurement to create an appropriately sized graft to repair the defect 12.

Figure 2A:
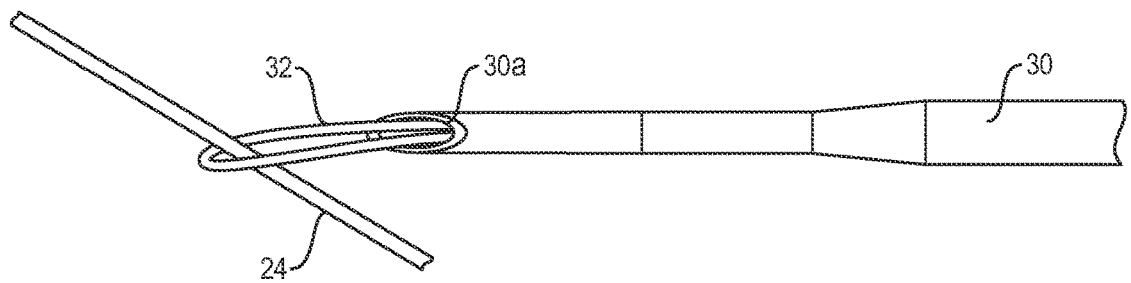
FIGS. 2A and 2B illustrate an alternative method of this disclosure for measuring the tissue defect.
Figure 2B:
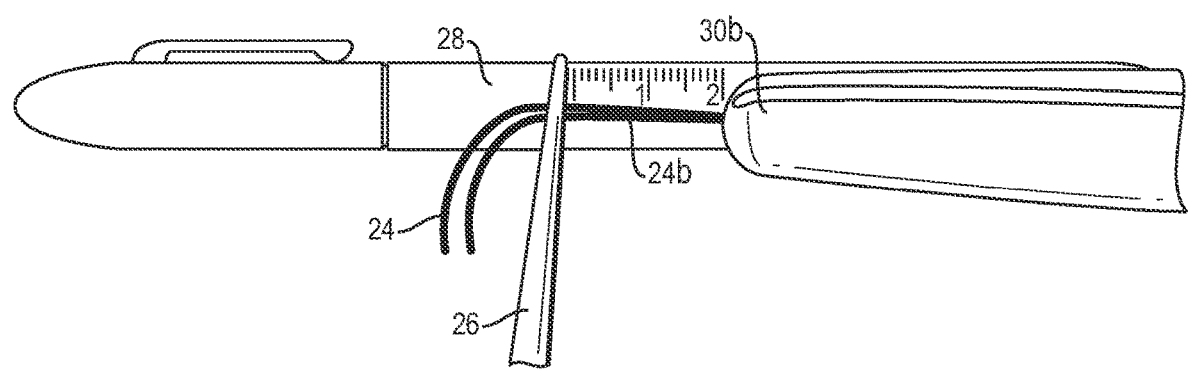

FIGS. 2A and 2B illustrate an alternative method for measuring the tissue defect 12. After securing the anchor 20 in the bone hole 18 (FIG. 1E), the surgeon can place the distal end 30a of secondary cannulated instrument 30, such as a suture passer (FIG. 2A), at the first end 12a of the defect 12. The surgeon extends a capture member 32 through the secondary instrument 30 to capture both free ends of the flexible strand 24. The surgeon then retrieves the flexible strands 24 through the instrument 30 such that the flexible strands 24 exit the proximal end 30b of the instrument 30 outside of the patient's body. Measuring now occurs in a similar fashion as that shown in FIGS. 1A-1I. That is, the surgeon places the distal end 30a of the instrument 30 at the second end 12b of the defect 12 such that a first portion 24a of the flexible strand 24 extends between the first end 12a and the second end 12b of the defect 12. The surgeon then attaches a clip member 26 to the flexible strands 24 extending from the instrument 30 at the proximal end 30b of the instrument 30 outside of the patient's body. The surgeon then places the distal end 30a of the instrument 30 back to the first end 12a of the defect 12 and tensions the flexible strands 24 at the proximal end 30b of the instrument 30. In this way, a second portion 24b of the flexible strand 24 extends between the proximal end 30b of the instrument 30 and the clip member 26 (FIG. 2B). This second portion 24b of the flexible strand 24 is equal in length to the first portion 24a. The surgeon can measure the second portion 24b with a measuring tool 28 and use this measurement to create an appropriately sized graft to repair the defect 12.

Figure 3A:
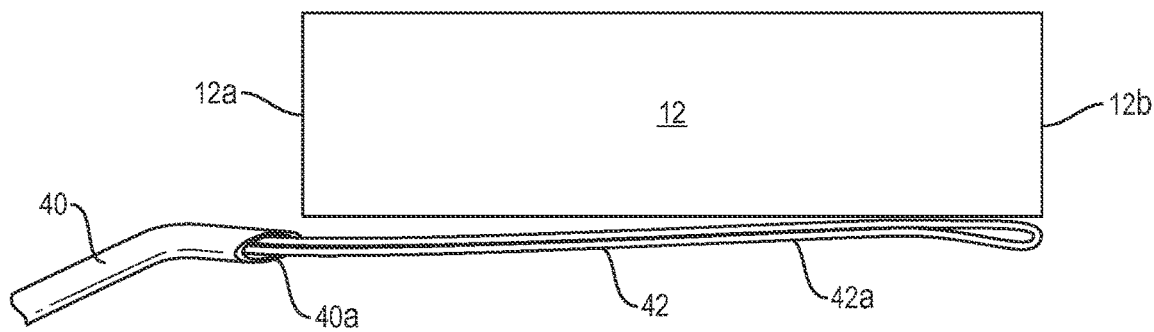
FIGS. 3A-C illustrate yet another method of this disclosure for measuring the tissue defect.
Figure 3B:
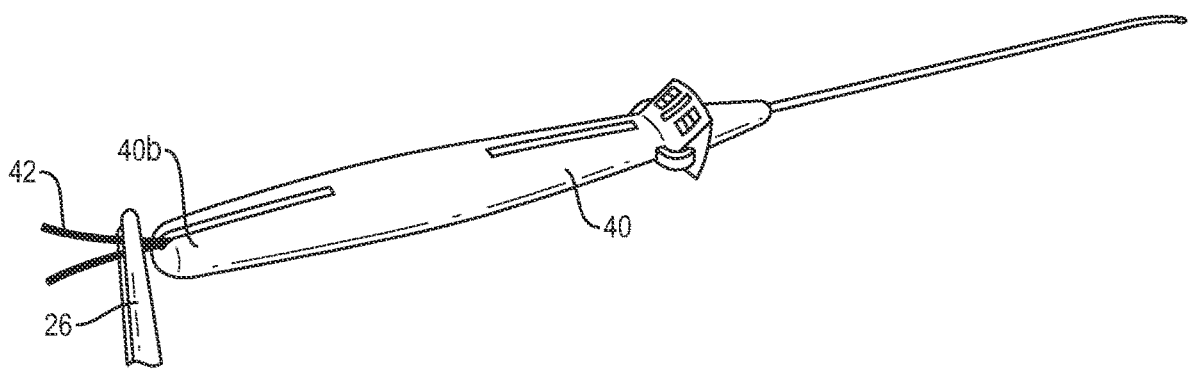
Figure 3C:
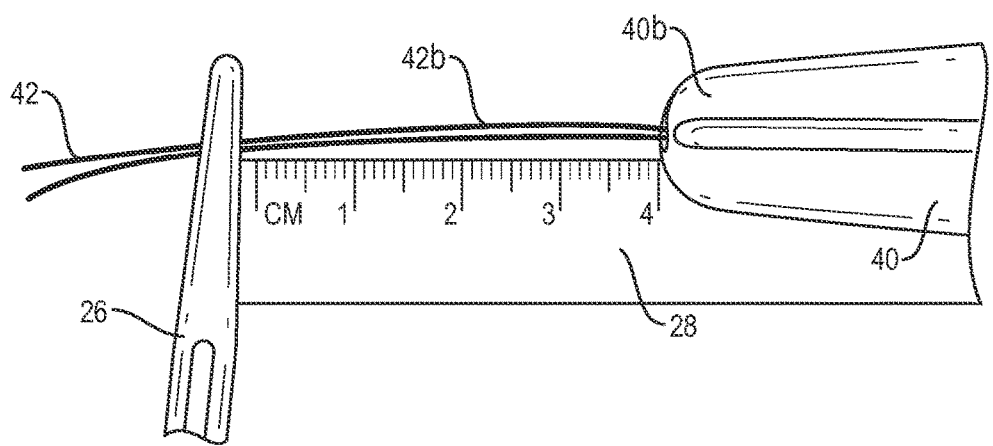

FIGS. 3A-C illustrate an alternative method for measuring the tissue defect 12. Before or after securing the anchor 20 in the bone hole 18, the surgeon can place the distal end 40a of secondary cannulated instrument 40, such as a suture passer (FIG. 3A), at the first end 12a of the defect 12. The surgeon extends a flexible member 42, such as a wire loop, through the secondary instrument 40 to the second end 12b of the defect 12b such that a first portion 42a of the flexible member 42 extends between the first end 12a and the second end 12b of the defect 12. Measuring now occurs in a similar fashion to that shown in FIGS. 1A-1I. That is, the surgeon attaches a clip member 26 to the flexible member 42 extending from the instrument 40 at the proximal end 40b of the instrument 40 outside of the patient's body (FIG. 3B). The surgeon can then pull the instrument 40 from the repair site and measure the length of the first portion 42a of the flexible member 42. Alternatively, as shown in FIG. 3C, the surgeon can pull the flexible member 42 at the proximal end 40b of the instrument 40. In this way, a second portion 42b of the flexible member 42 extends between the proximal end 40b of the instrument 40 and the clip member 26. This second portion 42b of the flexible member 42 is equal in length to the first portion 42a. The surgeon can measure the second portion 42b with a measuring tool 28 and use this measurement to create an appropriately sized graft to repair the defect 12.

While the disclosure particularly shows and describes preferred examples, those skilled in the art will understand that various changes in form and details may exist without departing from the spirit and scope of the present application as defined by the appended claims. The scope of this present application intends to cover such variations. As such, the foregoing description of examples of the present application does not intend to limit the full scope conveyed by the appended claims.

We claim:

1. A method of measuring a distance between first and second locations in tissue during a tissue repair, the method comprising:
   placing a distal end of a cannula against a first location in tissue, the first location being the site of a bone hole, an anchor comprising a body and a flexible strand being inserted into the bone hole such that the flexible strand extends from the body through the cannula and exits the proximal end of the cannula;
   placing the distal end of the cannula against a second location in the tissue such that a first portion of the flexible strand extends between the first location and the second location, the first portion of the flexible strand having a first length;
   attaching a clip member to the flexible strand at the proximal end of the cannula;
   replacing the distal end of the cannula against the first location;
   tensioning the flexible strand such that a second portion of the flexible strand extends between the proximal end of the cannula and the clip member, the second portion of the flexible strand having a second length equal to the first length; and
   using a measuring tool, determining a measurement of the second length, the measurement corresponding to a distance between the first and second locations in the tissue.

2. The method of claim 1, further comprising inserting the anchor through the cannula from a proximal end to the distal end of the cannula into the bone hole at the first location.

3. The method of claim 1, further comprising inserting a capture member through the cannula from a proximal end to the distal end of the cannula to retrieve the flexible strand through the cannula.

4. The method of claim 1, wherein the cannula comprises a drill guide.

5. The method of claim 1, wherein the cannula comprises a suture passer.

6. The method of claim 1, further comprising securing the body of the anchor in the bone hole.

7. The method of claim 6, wherein the body of the anchor comprises suture, and securing the body of the anchor in the bone hole comprises tensioning the flexible strand to change the body from a first configuration, in which a width of the body is less than a width of the bone hole, to a second configuration, in which the width of the body is greater than the width of the bone hole, forming an interference fit between the body and the bone hole.

8. The method of claim 1, wherein the flexible strand is a suture.

9. The method of claim 1, wherein the clip member is a needle driver or hemostat forceps.

10. The method of claim 1, wherein the measuring tool is a ruler or a graduated surgical marker.

11. The method of claim 1, wherein the first location is at a first end of a defect in the tissue and the second location is at a second end of the defect in the tissue.

12. A method of measuring a distance between first and second locations in tissue during a tissue repair, the method comprising:
   placing a distal end of a cannula against a first location in tissue;
   inserting a flexible member through the cannula from a proximal end to the distal end of the cannula such that a first portion of the flexible member extends from the first location to a second location in the tissue, the first portion of the flexible member having a first length;

attaching a clip member to the flexible member at the proximal end of the cannula;

pulling the flexible member through the cannula such that a second portion of the flexible member extends between the proximal end of the cannula and the clip member, the second portion of the flexible member having a second length equal to the first length; and using a measuring tool, determining a measurement of the second length, the measurement corresponding to a distance between the first and second locations in the tissue.

13. The method of claim 12, wherein the cannula comprises a suture passer.

14. The method of claim 12, wherein the flexible member is a wire loop.

15. The method of claim 12, wherein the clip member is a needle driver or hemostat forceps.

16. The method of claim 12, wherein the first location is at a first end of a defect in the tissue and the second location is at a second end of the defect in the tissue.

* * * * *